United States Patent [19]

Hajos

[11] 4,284,565

[45] Aug. 18, 1981

[54] TOTAL SYNTHESIS OF 1RS,4SR,5RS-4-(4,8-DIMETHYL)-5-HYDROXY-7-NONEN-1-YL)-4-METHYL-3,8-DIOXABICYCLO[3.2.1]OCTANE-1-ACETIC ACID AND RELATED COMPOUNDS

[75] Inventor: Zoltan G. Hajos, Princeton, N.J.

[73] Assignee: Ortho Pharmaceutical Corporation, Raritan, N.J.

[21] Appl. No.: 146,538

[22] Filed: May 2, 1980

[51] Int. Cl.³ .................................................. C07D 319/10
[52] U.S. Cl. .............................. 260/340.6; 260/343.6; 260/348.25; 562/532; 568/412; 568/418
[58] Field of Search ........................................ 260/340.6

[56] References Cited

U.S. PATENT DOCUMENTS

| | | | |
|---|---|---|---|
| 2,322,821 | 6/1943 | Brown | 260/340.6 |
| 2,771,471 | 11/1956 | De Groote | 260/340.6 |
| 4,102,895 | 7/1978 | Kanojia et al. | 260/340.6 |

*Primary Examiner*—Ethel G. Love
*Attorney, Agent, or Firm*—Benjamin F. Lambert

[57] ABSTRACT

The synthesis of 1RS,4SR,5RS-4-(4,8-dimethyl-5-hydroxy-7-nonen-1-yl)-4-methyl-3,8-dioxabicyclo[3.2.-1]octane-1-acetic acid and related compounds is described. The above acetic acid compound and its isomer are contragestational agents.

12 Claims, No Drawings

TOTAL SYNTHESIS OF 1RS,4SR,5RS-4-(4,8-DIMETHYL)-5-HYDROXY-7-NONEN-1-YL)-4-METHYL-3,8-DIOXABICYCLO[3.2.1]OCTANE-1-ACETIC ACID AND RELATED COMPOUNDS

The isolation and structural determination of zoapatanol, 2S,3R,6E-(2″-hydroxyethylidene)-2-methyl-2-(4′,8′-dimethyl-5′-oxo-7′-nonenyl)-oxepan-3-ol, one of the active ingredients in the zoapatle plant, is described in U.S. Pat. No. 4,086,358, issued Apr. 25, 1978. In U.S. Pat. No. 4,102,895, issued July 25, 1978, the preparation of 1RS,4SR,5RS-4-(4,8-dimethyl-5-hydroxy-7-nonen-1-yl)-4-methyl-3,8-dioxabicyclo[3.2.1]octane-1-acetic acid, a compound derived from zoapatanol, is described. The bicyclic derivative has the following formula:

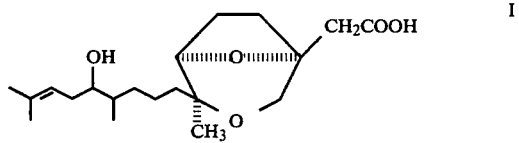

The present invention relates to a method of synthesizing 1RS,4SR,5RS-4-(4,8-dimethyl-5-hydroxy-7-nonen-1-yl)-4-methyl-3,8-dioxabicyclo[3.2.1]octane-1-acetic acid. This acetic acid derivative is active as a utero-evacuant agent. Many of the intermediates employed in the synthesis are novel compounds and are included as part of the invention.

The synthesis is comprised of several steps which are summarized in the following schematic diagram:

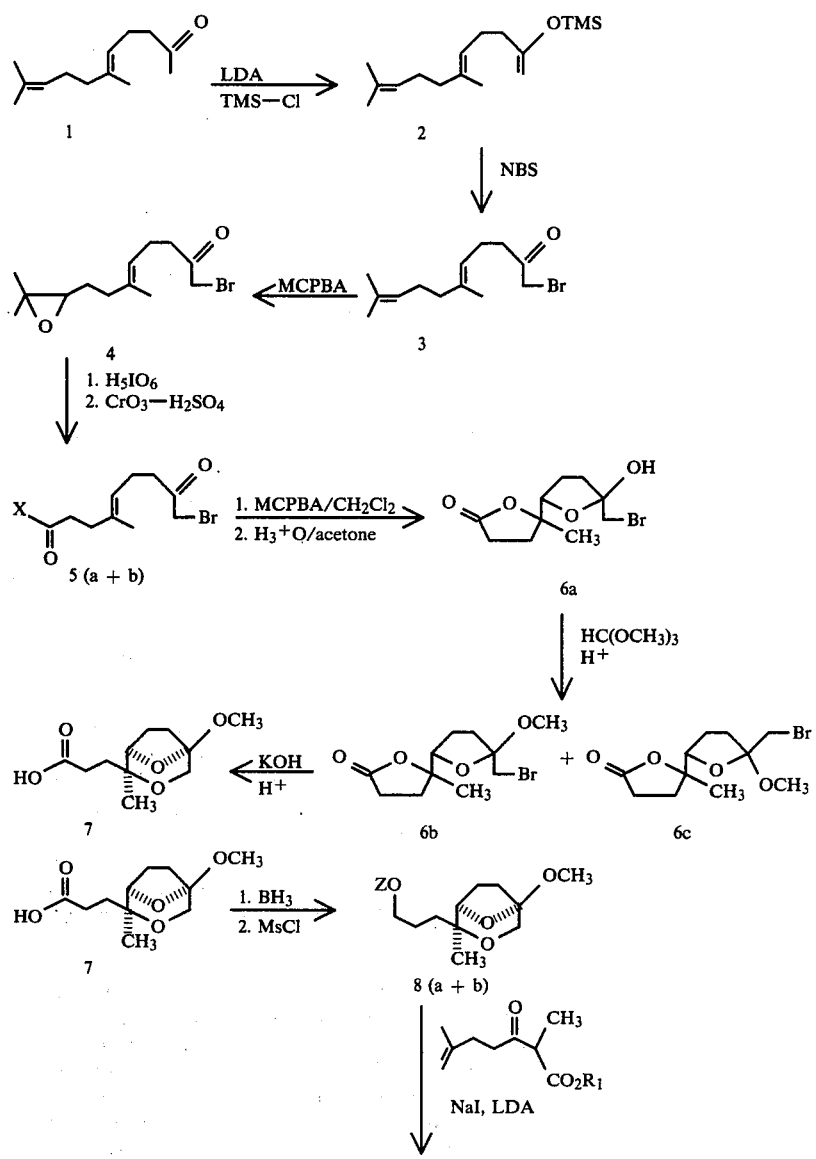

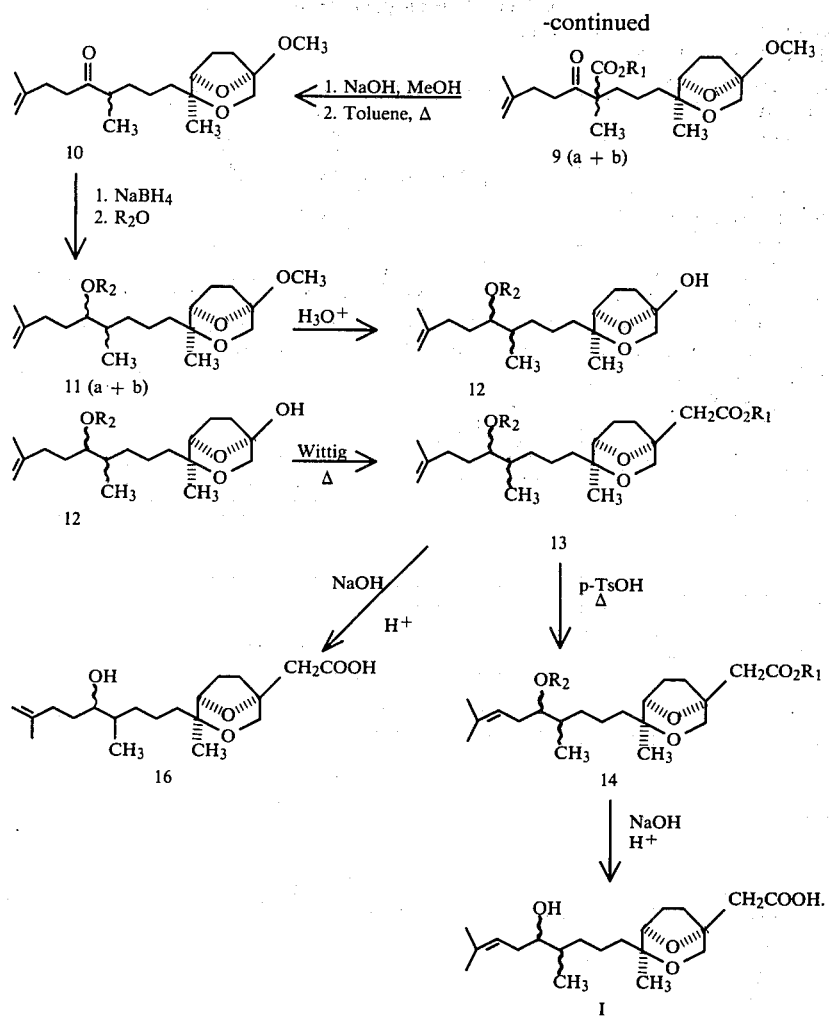

wherein X is hydrogen or hydroxy; Z is hydrogen or a mesyl group, $R_1$ is hydrogen or a lower alkyl group having 1-5 carbon atoms, $R_2$ is hydrogen or a lower acyl group having 2-5 carbon atoms, LDA is lithium diisopropylamide, TMS is trimethylsilyl group, NBS is N-bromosuccinimide and MCPBA is m-chloroperoxybenzoic acid.

As can be seen from the diagram, the first step in the synthesis involves the preparation of an enol silyl ether (2) by the reaction of geranyl acetone (1) with trimethylsilyl chloride in the presence of lithium diisopropylamide in a suitable solvent. The reaction is carried out preferably at a temperature between −80° C. and +15° C. The preferred reaction temperature is −70° C. Suitable solvents which can be employed include tetrahydrofuran, dioxane, diethyl ether and dimethoxyethane. The starting material (1) is prepared by the method of Stork & Burgstahler [Stork, G. and Burgstahler, A. W., J. Amer. Chem. Soc., 77, 5068 (1955)]. The enol silyl ether (2) is then reacted with a brominating agent such as N-bromosuccinimide to form the bromo-ketone (3). The reaction is carried out preferably at a temperature between −80° C. and 0° C. The preferred temperature is about −78° C. As the solent for the reaction tetrahydrofuran, dioxane diethyl ether and dimethoxyethane may be employed. Farnesol, citral, pseudoionine or linalool can also be employed as the starting material in the synthesis since they can be converted to geranyl acetone or one or more intermediates in the synthesis such as the bromo keto acid and aldehyde (5a and 5b).

The terminal double bond in the bromo-ketone (3) is then converted to the epoxide (4) by reaction with a peroxy acid such as, for example, m-chloroperoxybenzoic acid, peracetic acid, permaleic acid, perbenzoic acid, perphthalic acid and pertrifluroacetic acid in a suitable solvent such as, for example, methylene chloride, chloroform, and diethyl ether. The reaction is generally carried out at a temperature between −10° and 20° C. The preferred reaction temperature is 0° C. although room temperature may also be employed. The epoxide (4) is then converted to the corresponding aldehyde (5a, X=H) by reaction with periodic acid in an aqueous medium such as aqueous tetrahydrofuran, dioxane and dimethyoxyethane. Reaction of the aldehyde (5a) with Jones reagent yields the corresponding carboxylic acid (5b). The oxidation is carried out at a temperature between −10° C. and room temperature in a suitable solvent such as acetone, methylene chloride and chloroform. The preferred reaction temperature is 0° C. The acid is separated from the reaction mixture by techniques known to those skilled in the art.

The bromo-keto acid (5b) is converted to the cis-bromo hemiketal γ-lactone (6a) by reaction with a peroxy acid such as, for example, m-chloroperoxybenzoic acid, perbenzoic acid and perphthalic acid. The reaction is carried out at a temperature between 0° C. and room temperature in a suitable solvent such as, for example, methylene chloride, chloroform and ether. The preferred reaction temperature is about 2° C. The residue containing the cis-bromohemiketal γ-lactone (6a) is converted to a mixture of cis and trans ketals (6b and 6c) by reaction with trialkyl orthoformate such as trimethyl orthoformate and triethyl orthoformate in the presence of a strong anhydrous acid such as, for example, sulfuric acid, phosphoric acid, potassium acid sulfate and p-toluene sulfonic acid in an alcohol such as, for example, methanol or ethanol. The reaction can be carried out at a temperature between 0° C. and room temperature. The preferred temperature range is about 2°-5° C. The reaction can also be carried out in the absence of the trialkyl orthoformate.

The cis-bromo ketal (6b) in the mixture of cis/trans-bromo ketals (6b and 6c) is converted to the bicyclic ketal acid (7) by reaction with an alkaline hydroxide such as sodium hydroxide or potassium hydroxide in a highly polar aprotic solvent such as, for example, dimethylsulfoxide. The bicyclic ketal-acid (7) is converted to the 2-hydroxyethyl-3,8-dioxabicyclo[3.2.1]octane (8a, Z=H) by reaction with borane in a suitable solvent such as tetrahydrofuran. The reaction can be carried out at a temperature between 0° C. and room temperature. The bicyclic ketal mesylate (8b, Z=mesyl) is prepared by reacting the bicyclic hydroxyethyl compound (8a) with methanesulfonyl chloride in the presence of a tertiary amine such as, for example, triethylamine and pyridine. The reaction can be carried out at a temperature between 0° C. and room temperature. The preferred temperature range is about 0° C. to 5° C.

The bicyclic ketal mesylate (8b) is converted to the nonenyl-3,8-dioxabicyclo[3.2.1]octane (9a, $R_1$=alkyl) by first converting it to a halo derivative by reaction with a halide such as sodium iodide or lithium bromide and then reacting the halo derivative with ethyl 2,6-dimethyl-3-oxo-6-heptenoate in the presence of a strong alkali metal base such as sodium hydride, lithium diisopropylamide, potassium t-butoxide, sodamide, sodium methoxide and sodium ethoxide, for example, in a suitable solvent such as tetrahydrofuran dioxane, diethyl ether and dimethoxyethane.

The reaction is carried out at a temperature between 0° C. and room temperature. The preferred temperature range is 0° C. to 10° C. After removal of the solvents, anhydrous dimethylformamide is added to the reaction mixture and the -keto ester (9a, $R_1$=alkyl) is separated from the reaction mixture by techniques known to those skilled in the art.

The β-keto ester (9a) is then stirred in a basic aqueous-alcoholic solution until decarboxylation is achieved which results in the formation of the ketone (10). As the base an aqueous hydroxide such as aqueous sodium hydroxide or potassium hydroxide may be employed. The preferred alcohol is methanol. The β-keto acid (9b, R=H) obtained in part is decarboxylated to 9a by heating in a solvent such as toluene, benzene or cymene.

The ketone (10) is reduced to the corresponding alcohol (11a, $R_2$=H) by reduction with a ketone reducing agent such as sodium borohydride, lithium borohydride and lithium aluminum hydride in a suitable solvent such as, for example, ethanol, tetrahydrofuran and methanol. The reaction can be carried out at a temperature between 0° C. and room temperature. The preferred temperature range is 0° C. to 5° C.

The alcohol (11a) is converted to the corresponding ester (11b) by reaction with a carboxylic acid anhydride or acyl halide such as, for example, acetic anhydride, propionic anhydride, butyric anhydride, acetyl chloride, benzoyl chloride, etc., in the presence of a base such as pyridine or trimethylamine.

The hemiketal (12) is prepared by treating the ketal (11b) with a strong acid such as aqueous hydrochloric acid, sulfuric acid and phosphoric acid in a suitable solvent such as acetone, tetrahydrofuran or dioxane. The reaction is preferably carried out at a temperature between 30° C. and 60° C., although room temperature may also be employed.

The attachment of the last two carbon atoms in the structure of the zoapatanol derivative is accomplished by means of a Wittig reaction on the hemiketal (12) with (carbethoxymethylene)triphenylphosphorane at elevated temperatures to afford the ester (13). The reaction can be carried out at a temperature between 90° C. and 150° C., however, the preferred temperature range is 110° C. to 130° C.

Isomerization of the double bond in the side chain of the ester (13) to the 7-nonenyl isomer (14) is accomplished by treating the ester (13) with p-toluenesulfonic acid in a hydrocarbon solvent such as benzene or toluene. The reaction is preferably carried out at the reflux temperature of the solvent. The free acid (15), which is the subject of this invention is obtained by hydrolysis of the ester (14) according to techniques known to those skilled in the art.

Hydrolysis of the bicyclic ester (13) in a basic aqueous-alcoholic medium yields the free acid (16) which is the terminal double bond isomer of the zoapatanol derivative (15). Bases such as sodium hydroxide and potassium hydroxide may be employed. As the alcohol, ethanol, methanol and propanol may be employed. The isomer (16) possesses contragestational activity.

The following examples describe the invention in greater detail and are intended to be a way of illustrating but not limiting the invention.

EXAMPLE 1

6,10-Dimethyl-2-trimethylsilyloxy-5(E)-1,5,9-undecatriene (2)

Triphenylmethane indicator (50 mg) is added to diisopropylamine (distilled from lithium aluminum hydride; 6.5 mg, 0.046 M) dissolved in tetrahydrofuran (distilled from lithium aluminum hydride; 60 ml). The solution is cooled to −10° C. (ice-methanol bath), and n-butyllithium in hexane (18.7 ml of 2.4 M, 0.044 M) is added while stirring at −10° C. The resulting solution is kept at −10° C. for 20 minutes, and then at −70° C. for an additional 20 minutes. While stirring at −70° C., geranyl acetone (6.2 g, 0.032 M) dissolved in anhydrous tetrahydrofuran (6.0 ml) is added within about 15 minutes to the above solution followed by the addition via a cannula of a freshly prepared mixture of trimethylsilyl chloride (15 ml, 0.118 M) and triethylamine (2.6 ml, 0.018 M) in tetrahydrofuran (20 ml). After keeping the reaction mixture at −70° C. for 1.5 hours, solid NaHCO₃ is added, followed by a saturated aqueous NaHCO₃ solution (70 ml), also added at −70° C. During this addition, the temperature quickly rises to −10° C. and it is held at −10° C. with a dry ice-acetone bath. After the addition of the NaHCO₃ solution, the cooling bath is removed and a water bath is substituted. The two layers are separated and the aqueous layer is re-extracted with ether. The ether extracts are combined with the tetrahydrofuran layer and the solution is washed with saturated aqueous NaCl solution, dried with Na₂SO₄, filtered and evaporated in vacuo to afford crude 6,10-dimethyl-2-trimethylsilyloxy-5(E)-1,5,9-undecatriene (8.7 g) as a mobile yellow oil.

TLC (CH₂Cl₂): R_f=0.95; IR (neat): 1647, 1620, 1253, 849 cm⁻¹; NMR (CDCl₃δ): 5.10 (m, 2H. olefinic protons); 4.02 (s, 2H,

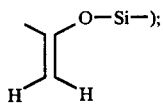

2.03 (m, 8H, —CH₂—CH₂—); 1.68 (br. s, 3H,

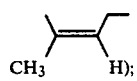

1.62 (br sm 6H,

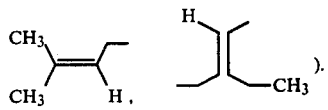

EXAMPLE 2

1-Bromo-6,10-dimethyl-5(E)-5,10-undecadien-2-one (3)

Anhydrous solid NaHCO₃ (3.3 g) is added to crude 6,10-dimethyl-2-trimethylsilyloxy-5(E)-1,5,9-undecatriene (8.7 g, 0.032 M) dissolved in tetrahydrofuran (170 ml) with stirring. The mixture is cooled to −78° C. under nitrogen, and solid N-bromosuccinimide (6.04 g, 0.034 M) is added. The reaction mixture is stirred at −78° C. for 2 hours and then poured into a stirred mixture of ice-cold 10% aqueous NaHCO₃ solution and ether. The organic layer is separated, washed with 10% aqueous Na₂SO₄ solution, saturated, aqueous NaCl, dried with Na₂SO₄, filtered and evaporated in vacuo to afford 1-bromo-6,10-dimethyl-5(E)-5,10-undecadien-2-one as a brown oil (8.6 g, 98.4%).

TLC (CH₂Cl₂): R_f=0.90; IR (neat): 1724, 845 cm⁻¹: NMR (CDCl₃,δ): 5.01 (m, 2H, vinyl protons); 3.85 (s, 2H,

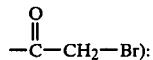

2.55 (m, 2H,

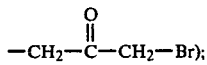

2.28–1.96 (m, 6H, methylenes allylic to double bond); 1.66 (m, 3H, cis vinyl methyl); 1.61 (m, 6H, trans vinyl methyls).

EXAMPLE 3

1-Bromo-6,10-dimethyl-9,10-oxido-5(E)-undecen-2-one (4)

Water (250 ml) and saturated NaHCO₃—H₂O (250 ml) are added to 1-bromo-6,10-dimethyl-5(E)-5,10-undecadien-2-one (31.5 g, 0.115 M) dissolved in CH₂Cl₂ (500 ml). A solution of m-chloroperoxybenzoic acid (MCPBA; 22.0 g, 0.127 M) dissolved in CH₂Cl₂ (500 ml) is added to the stirred mixture at +20° C. dropwise within 3 hours. The CH₂Cl₂ layer is separated, washed with NaCl—H₂O, dried with Na₂SO₄, filtered and evaporated in vacuo to afford crude 1-bromo-6,10-dimethyl-9,10-oxido-5(E)-undecen-2-one (33.3 g).

TLC (Et₂O): R_f=0.77; NMR (CDCl₃, δ): 5.08 (m, 1H, vinyl proton); 3.87 (s, 2H,

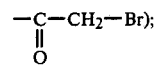

2.68 (t, 1H, 9-H); 1.67 (br. s, 3H, 6(E)CH₃); 1.30 (s, 3H, 10(Z)CH₃); 1.27 (s, 3H, 10(E)CH₃).

The crude product is used without further purification in the next step.

EXAMPLE 4

1-Bromo-6-methyl-2-oxo-5(E)-nonen-9-al (5a)

Periodic acid (34.6 g, 3×0.051 M) dissolved in aqueous tetrahydrofuran (240 ml, 5% by volume) is added to crude 1-bromo-6,10-dimethyl-9,10-oxido-5(E)-undecen-2-one (14.7 g, 0.051 M) in aqueous tetrahydrofuran (240 ml, 5% by volume) while stirring at 20° C. over a 3 minute period and the mixture is stirred at 20° C. for an additional 9 minutes. The reaction mixture is then added to a stirred mixture of ice cold saturated NaHCO₃—H₂O (400 ml) and ether (700 ml). The mixture is filtered, the organic layer is separated, washed with 10% NaHCO₃—H₂O, NaCl—H₂O, dried with Na₂SO₄, filtered and concentrated in vacuo to give crude 1-bromo-6-methyl-2-oxo-5(E)-nonen-9-al (14.5 g).

TLC (10% ether in CH₂Cl₂): R_f=0.52; IR (neat): 2730 (CH of aldehyde), 1706 cm⁻¹ (broad CO groups).

The crude reaction product is used without further purification in the next step.

EXAMPLE 5

1-Bromo-6-methyl-2-oxo-5(E)-nonen-9-oic acid (5b)

Jones reagent (20 ml) is added to 1-bromo-6-methyl-2-oxo-5(E)-nonen-9-al (14.5 g, 0.059 M of ~38% pure) in acetone (250 ml) within 5 minutes while stirring at 0° C. The resultant solution is stirred for an additional 10 minutes at 0° C. and then added to a stirred solution of ice cold saturated NaHCO₃—H₂O (350 ml). The acetone is removed in vacuo, CH₂Cl₂ (300 ml) is added, and the mixture is filtered. The organic phase is washed with H₂O and then added to the NaHCO₃—H₂O. The aqueous basic solution is washed once with CH₂Cl₂ and once with ether, stirred at 0° C. and acidified carefully with ice cold 6 N HCl—H₂O to pH=2.0. The acidic solution is then extracted twice with CH₂Cl₂ and once with ether. The extracts are washed separately with NaCl—H₂O, combined, dried with Na₂SO₄, filtered, and evaporated in vacuo to give 1-bromo-6-methyl-2-oxo-5(E)-nonen-9-oic acid (3.92 g, 29.3%). The compound solidifies on standing.

TLC (Et₂O): R_f=0.67; IR (neat): 2700–2330 (OH), 1710 cm⁻¹ (CO). NMR (CDCl₃, δ): 8.67 (br, 1H, —CO₂H), 5.17 (t, 1H, vinylic H), 3.88 (s, 2H, —CO—CH₂—Br), 1.67 (br. s, 3H, vinylic CH₃).

EXAMPLE 6

Cis/trans 2-(2-bromomethyl-2-methoxytetrahydrofuran-5-yl-2-methyl-5-oxotetrahydrofuran (6b and 6c)

Metachloroperoxybenzoic acid (1.40 g, 8.1 mM) in $CH_2Cl_2$ (20 ml) is added to 1-bromo-6-methyl-2-oxo-5(E)-nonen-9-oic acid (2.2 g, 8.4 mM) in $CH_2Cl_2$ (15 ml) at 2° C. dropwise, while stirring over a fifteen minute period. Stirring at 2° C. is continued for three hours. Acetone (50 ml) and 0.2 N HCl—$H_2O$ (10 ml) are added at 2° C. to the above stirred mixture and stirring is continued at approximately 5° C. for 16 hours. The solvents are evaporated in vacuo with no external heating. The residue is extracted with $CH_2Cl_2$ and the extract is washed with NaCl—$H_2O$ containing enough $NaHCO_3$—$H_2O$ to make it basic, and then with saturated NaCl—$H_2O$ to a neutral pH. The extract is then dried with $Na_2SO_4$, filtered, and evaporated in vacuo to give an oily solid (3.9 g). A small sample of the mixture is dissolved in $CH_2Cl_2$, and extracted twice with saturated $NaHCO_3$—$H_2O$. The extract is then washed with NaCl—$H_2O$, dried with $Na_2SO_4$, filtered and evaporated in vacuo to give the cis bromo hemiketal γ-lactone 2-(2-bromomethyl-2-hydroxytetrahydrofuran-5-yl)-2-methyl-5-oxotetrahydrofuran.

TLC (10% ether in $CH_2Cl_2$): $R_f=0.11$. IR (neat): 3300 (OH), 1754 cm$^{-1}$ (CO). NMR ($CDCl_3$, δ): 4.23 (m, 1H,

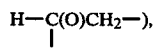

3.53 (s, 2H, —$CH_2$—Br), 2.05–3.00 (m, 8H, —CO—$CH_2CH_2$— and

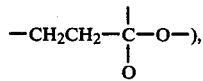

1.38 (s, 3H, $CH_3$—).

The crude main batch (~3.9 g) is dispersed in trimethyl orthoformate (4.0 ml). The dispersion is stirred under nitrogen at 2° C. and ~0.1 N $H_2SO_4$-methanol (1.4 ml of 0.27 ml conc. $H_2SO_4$ in 100 ml methanol) is added with a syringe through the serum cap. The reaction mixture is stirred at approximately 5° C. for 2 days. The reaction mixture is then added dropwise to a stirred, ice cold mixture of saturated $NaHCO_3$—$H_2O$ (20 ml) and $CH_2Cl_2$ (20 ml). The organic layer is washed with saturated $NaHCO_3$—$H_2O$, and then with NaCl—$H_2O$. It is then dried with $Na_2SO_4$, filtered, and concentrated in vacuo to give a mixture of cis/trans bromo ketal lactones 2-(2-bromomethyl-2-methoxytetrahydrofuran-5-yl)-2-methyl-5-oxotetrahydrofuran (approximately 60/40 by GC/MS, 1.94 g).

TLC (10% $Et_2O/CH_2Cl_2$): $R_f=0.30$. IR (neat): 1770 (broad), 1709 (sh), 1087, 1041 cm$^{-1}$ (ether bonds). NMR ($CDCl_3$, δ): 4.14 (m, 1H,

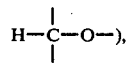

3.64 (s, ~60% of 2H, —$CH_2Br$), 3.49 (s, ~40% of 2H, $CH_2Br$), 3.29 (s, ~40% of 3H, —$OCH_3$), 3.23 (s, ~60% of 2H, $CH_2Br$). GC/MS=two identical spectra, ratio ~60/40. M+ (292/294), M+ —$OCH_3$=261/263. BP=71

EXAMPLE 7

1RS,4RS,5SR-4-(2-Carboxyethyl)-1-methoxy-4-methyl-3,8-dioxabicyclo[3.2.1]octane (7)

Potassium hydroxide pellets (6 g, 0.11 M) are added to the cis/trans mixture of the bromo ketal lactones (3.27 g, 11.2 mM) in anhydrous dimethylsulfoxide (25 ml). The mixture is stirred and heated at 45° C. under nitrogen for three days. It is then cooled to room temperature and $CH_2Cl_2$ (100 ml) is added. The organic layer is decanted and the KOH pellets are quickly rinsed with ice water (60 ml). The rinse is added to the organic extract and the light yellow organic phase is re-extracted two times with ice water (2×20 ml) and then with NaCl—$H_2O$ (20 ml). The dark, aqueous basic solution is cooled with ice water, stirred, acidified with 6 N HCl—$H_2O$ and the acidic solution is extracted with $CH_2Cl_2$ (~50 ml). The aqueous layer is re-acidified with 2 N HCl—$H_2O$ (~2.0 ml) and re-extracted with $CH_2Cl_2$ (2×50 ml). The $CH_2Cl_2$ extracts are combined and washed free of acid with NaCl—$H_2O$. The slightly turbid aqueous layer is re-extracted with ether and washed with NaCl—$H_2O$. The $CH_2Cl_2$ and ether solutions are combined, dried with $Na_2SO_4$, filtered, and evaporated in vacuo to give a mixture of 1RS,4RS,5SR-4-(2-carboxyethyl)-1-methoxy-4-methyl-3,8-dioxabicyclo[3.2.1]octane and the non-cyclized trans bromo ketal lactone 2-(2-bromomethyl-2-methoxytetrahydrofuran-5-yl)-2-methyl-5-oxotetrahydrofuran (6c, 2.02 g of mixture). The mixture (2 g) is dissolved in ether (50 ml) and the ether solution is extracted with saturated $NaHCO_3$—$H_2O$ (2×20 ml and 1×10 ml). The combined $NaHCO_3$—$H_2O$ extracts are re-extracted with ether (3×20 ml). The combined ether extracts are evaporated in vacuo to give crude trans bromo ketal lactone (640 mg). The aqueous $NaHCO_3$—$H_2O$ is re-extracted with $CH_2Cl_2$ and then with ether. These neutral $CH_2Cl_2$ and ether extracts are added to the crude residue obtained above and the solvent is evaporated in vacuo to give the crude trans bromo ketal lactone 2-(2-bromomethyl-2-methoxytetrahydrofuran-5-yl)-2-methyl-5-oxotetrahydrofuran (6c, 660 mg, 20%).

TLC (10% ether in $CH_2Cl_2$): $R_f=0.3$. TLC (ether; $R_f=0.4$. IR (neat) 1754 cm$^{-1}$ (broad). NMR ($CDCl_3$, δ): 4.62 (t, J=8 Hz, 1H,

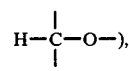

3.5 (q, J=12 Hz, 2H, —$CH_2$—Br), 1.37 (s, 3H,

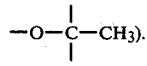

The NaHCO₃—H₂O extract is cooled with ice water, stirred, acidified carefully with 6 N HCl—H₂O and then extracted with CH₂Cl₂ (2×50 ml) and ether (1×50 ml). The extracts are washed separately free of mineral acid with saturated NaCl—H₂O, combined, dried with Na₂SO₄, filtered, and evaporated in vacuo to give 1RS,4RS,5SR-4-(2-carboxyethyl)-1-methoxy-4-methyl-3,8-dioxabicyclo[3.2.1]octane (1.2 g, 46.6%), which solidifies on standing.

TLC (10% ether in CH₂Cl₂): $R_f$=0.1. TLC (ether): $R_f$=0.6. IR (neat) 2800–2500 (OH), 1715 (br, CO) cm⁻¹. NMR (CDCl₃, δ): 10.0 (br, 1H, CO₂H̲), 3.93 (t, 1H,

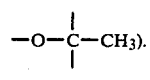

3.53 (q, J=12 Hz, 2H,

—O—CH₂—C(O)OCH₃), 3.43 (s, 3H, —OCH₃), 1.37 (s, 3H,

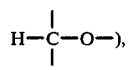

GC/MS of TMS derivative (C.I. mode): (M+1)⁺ 303; BP 213 (M+1-TMSOH).

EXAMPLE 8

1RS,4RS,5SR-4-(2-Hydroxyethyl)-1-methoxy-4-methyl-3,8-dioxabicyclo[3.2.1]octane (8a)

BH₃·THF (20 ml of approximately 1 molar solution) is added to 1RS,4RS,5SR-4-(2-carboxyethyl)-1-methoxy-4-methyl-3,8-dioxabicyclo[3.2.1]octane (3.13 g, 13.6 mM) in anhydrous tetrahydrofuran (30 ml) while stirring at 2° C. under nitrogen within three minutes. Stirring is continued for thirty minutes at 2° C. and at room temperature for two hours after which the solution is added dropwise, carefully, while stirring, to ice water (20 ml). The aqueous solution is extracted with CH₂Cl₂ and with ether and the combined extracts are concentrated in vacuo. The residue is dissolved in CH₂Cl₂ and the solution is washed with saturated NaCl—H₂O containing enough saturated NaHCO₃—H₂O to make it basic. The extract is washed with saturated NaCl—H₂O, dried with Na₂SO₄, filtered, and evaporated in vacuo to give 1RS,4RS,5SR-4-(2-hydroxyethyl)-1-methoxy-4-methyl-3,8-dioxabicyclo[3.2.1]octane (2.94 g, 100%).

TLC (ether): $R_f$=0.20. IR (neat) 3330 (OH), 1060 1040 cm⁻¹ (ether bands). NMR (CDCl₃, δ): 3.92 (m, 1H,

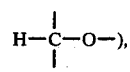

3.63 (m, 2H, HO—CH̲₂—), 3.5 (q, 2H, —O—CH̲₂—C(O)—OCH₃): 3.40 (s, 3H, —OCH̲₃), 1.37 (s, 3H,

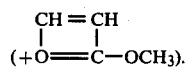

GC/MS: M⁺216. BP 85

$$\begin{matrix} CH=CH \\ | \quad\quad | \\ (+O\!\!=\!\!\!=\!\!C-OCH_3). \end{matrix}$$

EXAMPLE 9

1RS,4RS,5SR-4-(2-Methanesulfonyloxypropyl)-1-methoxy-4-methyl-3,8-dioxabicyclo[3.2.1]octane (8b)

Triethylamine (4.0 ml, 27 mM distilled, stored over CaH₂) is added to 1RS,4RS,5SR-4-(2-hydroxyethyl)-1-methoxy-4-methyl-3,8-dioxabicyclo[3.2.1]octane (2.94 g, 13.6 mM) in CH₂Cl₂ (30 ml). The resultant mixture is cooled with ice water, stirred under nitrogen and methanesulfonyl chloride (1.8 ml, 22.40 mM) is added dropwise within five minutes. The reaction mixture is stirred at 5° C. under nitrogen for sixteen hours and then added dropwise to a stirred mixture of ice water (30 ml) and 2 N HCl—H₂O (4.0 ml). The organic layer is separated, washed with saturated NaCl—H₂O (2×20 ml), dried with Na₂SO₄, filtered, and evaporated in vacuo to give 1RS,4RS,5SR-2-(2-methanesulfonyloxypropyl)-1-methoxy-4-methyl-3,8-dioxabicyclo[3.2.1]octane (3.29 g, 82.3%).

TLC (ether): $R_f$=0.4. IR (neat): 1330, 1190, 1150 (OSO₂ bands), 1090, 1060 cm⁻¹ (ether bands). NMR (CDCl₃, δ): 4.23 (m, 2H, CH₃SO₂O—CH̲₂—CH₂—), 3.87 (t, 1H,

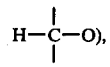

3.53 (q, 2H,

—OCH₂—C(O)OCH₃), 3.02 (s, 3H, CH̲₃SO₂O—). GC/MS: M⁺ (294), M⁺ —CH₂O=264, BP=86

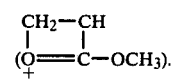

EXAMPLE 10

1RS,4RS,5SR-1-Methoxy-4-methyl-4-(4-carbethoxy-4,8-dimethyl-5-oxo-8-nonenyl)-3,8-dioxabicyclo[3.2.1]octane (9a)

The bicyclic ketal mesylate obtained in Example 9 above (458 mg, 1.56 mM) is added to sodium iodide (254 mg, 1.6 mM of Fisher, certified, with the exclusion of moisture, under nitrogen) followed by the addition of ethyl, 2,6-dimethyl-3-oxo-6-heptenoate (0.75 ml, 3.0 mM). Anhydrous tetrahydrofuran (4 ml) is added to the slowly stirred mixture and the mixture is cooled to 0° C. A solution of lithium diisopropylamide in hexane (3 ml of approximately 0.7 molar=2.1 mM) is added dropwise to this mixture under nitrogen. The mixture is allowed to come to 20° C. and is stirred at room temperature for one day. The solvents are removed by evaporation with a fast stream of nitrogen at room temperature. Anhydrous dimethylformamide (4.0 ml) is added to the residue and the stirring at room temperature under nitrogen is continued for 72 hours. $CH_2Cl_2$ (25 ml) and ice water (20 ml) are added and the organic layer is separated, washed with water containing enough 2 N HCl—$H_2O$ to make it acidic. The organic layer is washed with saturated NaCl—$H_2O$, dried with $Na_2SO_4$, filtered and evaporated in vacuo to give the crude β-keto ester (1.3 g) which is chromatographed on a SilicAR CC-7 column (30 g). Elution with $CH_2Cl_2$ (400 ml), 5% ether in $CH_2Cl_2$ (250 ml), ether (200 ml) in approximately 75 ml fractions gives a total recovery of 927 mg. Fractions 7-10 (5% ether in $CH_2Cl_2$ eluent) contain 1RS,4RS,5SR-1methoxy-4-methyl-4-(4-carbethoxy-4,8-dimethyl-5-oxo-8-nonenyl)-3,8-dioxabicyclo[3.2.1]octane (418 mg, 65%).

TLC (10% ether in $CH_2Cl_2$): $R_f$=0.30. IR (neat) 1730 (ester 10), 1709 (keto CO) and 1644 cm$^{-1}$ (olefinic double bond). NMR (CDCl$_3$, δ): 4.67 (m, 2H,

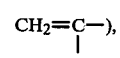

4.17 (q, J=7 Hz, 2H, —OC$\underline{H}_2$CH$_3$), 3.87 (m, 1H,

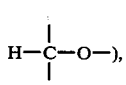

3.50 (q, 2H, —O—C$\underline{H}_2$—C(O)OCH$_3$), 3.40 (s, 3H, —OC$\underline{H}_3$), 1.72 (br s, 3H,

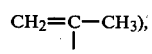

1.33 (s, 3H,

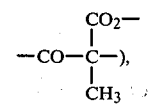

1.32 (t, J=7 Hz, 3H, —OCH$_2$C$\underline{H}_3$), 1.30 (s, 3H,

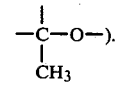

EXAMPLE 11

1RS,4RS,5SR-1-Methoxy-4-methyl-4-(4,8-dimethyl-5-oxo-8-nonenyl)-3,8-dioxabicyclo[3.2.1]octane (10)

Aqueous sodium hydroxide (10 ml) is added to the β-keto ester obtained in Example 10 above (2.24 g, 5.7 mM) in methanol (10 ml) with stirring at 2° C. under nitrogen. After ten minutes of stirring, the mixture is allowed to come to room temperature and the stirring is continued for four days under nitrogen. The methanol is then evaporated in vacuo and the aqueous residue is extracted with $CH_2Cl_2$. The $CH_2Cl_2$ extract is washed with saturated NaCl—$H_2O$, dried with $Na_2SO_4$, filtered and evaporated in vacuo to give 1RS,4SR,5SR-1-methoxy-4-methyl-4-(4,8-dimethyl-5-oxo-8-nonenyl)-3,8-dioxabicyclo[3.2.1]octane (1.33 g, 72%).

TLC (10% ether in $CH_2Cl_2$): $R_f$=0.30. IR (neat) 1709 (keto CO), 1658 (double bond), 1060–1090 cm$^{-1}$ (ether bonds). NMR (CDCl$_3$, δ): 4.67 (m, 2H,

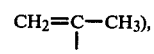

3.93 (m, 1H,

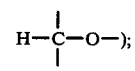

3.50 (q, J=12 Hz, 2H, —O—C$\underline{H}_2$—C(O)OCH$_3$), 3.37 (s, 3H, —OC$\underline{H}_3$), 1.73 (br s, 3H, CH$_2$=

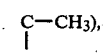

1.32 (s, 3H,

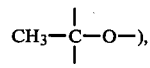

1.06 (d, J=7 Hz, 3H,

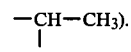

GC/MS: M+ 324; M—CH$_2$O=294. BP=86

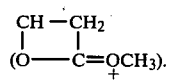

The aqueous basic solution obtained after the separation from the $CH_2Cl_2$ is cooled to 2° C., stirred, and acidified carefully with ice-cold 6 N HCl—$H_2O$ (approximately 3.0 ml). The acidic solution is extracted with CH₂Cl₂ and with ether and the organic extracts are washed separately with NaCl—H₂O, combined, dried with Na₂SO₄, filtered, and evaporated in vacuo to give 1RS,4SR,5SR-1-methoxy-4-methyl-4-(4,8-dimethyl-5-oxo-8-nonenyl)-3,8-dioxabicyclo[3.2.1]octane-4-carboxylic acid (9b, 0.41 g, 19.6%).

TLC (10% ether in CH₂Cl₂): R_f=0.15 (streak). IR (neat): 3600–3300 (OH), 2800–3550 (OH), 1710 (CO), 1665 cm⁻¹. NMR (CDCl₃, δ): 4.67 (m, 2H,

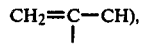

3.93 (m, 1H,

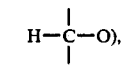

3.50 (q, J=12 Hz, 2H, —O—CH₂—C(0)CH₃), 3.42 (s, 3H, —OCH₃), 1.75 (br s,

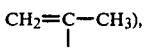

1.40 (s, 3H,

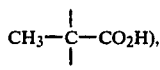

1.35 (s, 3H,

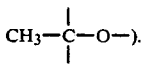

The β-keto acid obtained above (0.41 g) is decarboxylated by refluxing it in anhydrous toluene (80 ml) under nitrogen for two hours to give the ketone 1RS,4RS,5SR-1-methoxy-4-methyl-4-(4,8-dimethyl-5-oxo-8-nonenyl)-3,8-dioxabicyclo[3.2.1]octane (0.35 g, 98.4%). This sample of the ketone is identical (TLC, IR, NMR, GC/MS) to the sample of the ketone obtained above.

EXAMPLE 12

1RS,4RS,5SR-1-Methoxy-4-methyl-4-(5-hydroxy-4,8-dimethyl-8-nonenyl)-3,8-dioxabicyclo[3.2.1]octane (11a)

NaBH₄ (378 mg, 10 mM) is added in small portions within three minutes to 1RS,4RS,5SR-1-methoxy-4-methyl-4-(4,8-dimethyl-5-oxo-8-nonenyl)-3,8-dioxabicyclo[3.2.1]octane (1.33 g, 4.1 mM) in absolute ethyl alcohol (10 ml) while stirring at 0° C. under nitrogen. The mixture is stirred in the cold for two hours and then added dropwise to ice water (15 ml) with stirring. The aqueous mixture is carefully acidified with 6 N HCl—H₂O and the acidic solution is extracted with ether (3×30 ml). The extract is washed with saturated NaCl—H₂O (10 ml) containing a few drops of saturated NaHCO₃—H₂O to make it basic. The ether is evaporated in vacuo and the residue is dissolved in CH₂Cl₂, washed with NaCl—H₂O, dried with Na₂SO₄, filtered, and evaporated in vacuo to give 1RS,4RS,5SR-1-methoxy-4-methyl-4-(5-hydroxy-4,8-dimethyl-8-nonenyl)-3,8-dioxabicyclo[3.2.1]octane (1.25 g, 93.5%).

TLC (ether): R_f=0.76; IR (neat): 3350 (OH), 1090–1060 cm⁻¹ (ether bonds). NMR (CDCl₃, δ): 4.68 (br s, 2H,

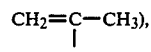

3.91 (m, 1H,

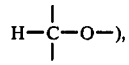

3.5 (q, J=11 Hz, 2H,

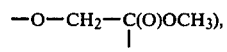

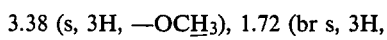

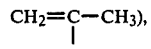

3.38 (s, 3H, —OCH₃), 1.72 (br s, 3H,

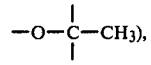

1.31 (s, 3H,

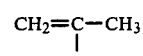

1.18 (d, J=7 Hz, 1H, —CH—CH₃). GC/MS of TMS derivative (C.I. mode): (M+1)⁺=399, 399−TMSO=310 (BP).

EXAMPLE 13

1RS,4RS,5SR-1-Methoxy-4-methyl-4-(5-acetoxy-4,8-dimethyl-8-nonenyl)-3,8-dioxabicyclo[3.2.1]octane (11b)

A mixture of anhydrous pyridine (1.5 ml) and acetic anhydride (3.0 ml) is added to the ketal alcohol (1.25 g, 3.83 mM) obtained in Example 12 above at room temperature under nitrogen. The mixture is stirred at room temperature for sixteen hours after which the solution is evaporated while stirring under high vacuum at 45° C. for one hour. The residue obtained is dissolved in CH₂Cl₂ and the resulting solution is washed with saturated NaCl—H₂O containing 2 N HCl—H₂O. The solution is then washed with saturated NaCl—H₂O, dried with Na₂SO₄, filtered and evaporated in vacuo to give 1RS,4RS,5SR-1-methoxy-4-(5-acetoxy-4,8-dimethyl-8-nonenyl)-3,8-dioxabicyclo[3.2.1]octane (1.4 g, 99.3%).

TLC (10% ether in CH₂Cl₂): R_f=0.65. IR (neat): 1739 (CO), 1242 (acetate), 1090–1030 cm⁻¹ (ether bonds). NMR (CDCl₃, δ): 4.68 (br, 3H,

CH₂=C—CH₃ and —C<u>H</u>—OCOCH₃), 3.91 (m, 1H,

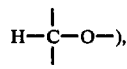

3.5 (q, J=11 Hz, 2H, —O—C<u>H</u>₂—C(O)OCH₃), 3.38 (s, 3H, —OC<u>H</u>₃), 2.03 (s, 3H, —OCOC<u>H</u>₃), 1.72 (br s, 3H, CH₂=C—C<u>H</u>₃), 1.31 (s, 3H, C<u>H</u>₃—C—O—), 1.18 (d, J=7 Hz, 3H,

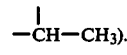

GC/MS: M⁺ 368, M—CH₂O=338, M—HOAc=308, BP=86

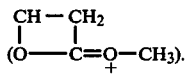

EXAMPLE 14

1RS,4RS,5SR-1-Hydroxy-4-methyl-4-(5-acetoxy-4,8-dimethyl-8-nonenyl)-3,8-dioxabicyclo[3.2.1]octane (12)

1 N HCl-H₂O (4 ml) is added to 1RS,4RS,5SR-1-methoxy-4-(5-acetoxy-4,8-dimethyl-8-nonenyl)-3,8-dioxabicyclo[3.2.1]octane (1.4 g, 3.8 mM) in acetone (12 ml). The mixture is stirred and heated at 55° C. for four hours. The acetone is evaporated in vacuo at room temperature, the residue is extracted with CH₂Cl₂ and washed with saturated NaCl—H₂O containing enough saturated NaHCO—H₂O to make it basic, and then with NaCl—H₂O. The solution is dried with Na₂SO₄, filtered, and evaporated in vacuo to give 1RS,4RS,5SR-1-hydroxy-4-methyl-4-(5-acetoxy-4,8-dimethyl-8-nonenyl)-3,8-dioxabicyclo[3.2.1]octane (1.23 g, 91.4%).

TLC (10% ether in CH₂Cl₂): R$_f$=0.15. IR (neat) 333 (OH), 1725 (CO), 1242 cm⁻¹ (acetate). NMR (CDCl₃,δ): 4.80 (m, 1H,

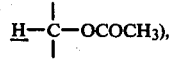

4.72 (br, 2H, C<u>H</u>₂=C—CH₃), 3.97 (m, 1H,

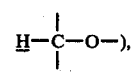

3.58 (q, 2H,

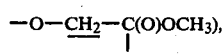

2.07 (s, 3H, —O—CO—C<u>H</u>₃), 1.75 (br s, 3H,

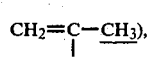

1.35 (s, 3H,

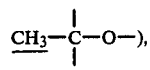

0.87 (d, J=7 Hz, 3H, —CH—C<u>H</u>₃). GC/MS of TMS derivative: M⁺ (426⎯⎯⎯→366; 366—CH₂O=336; 336—CH₂= —HOAc

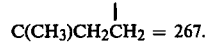

BP=73 (TMS).

EXAMPLE 15

Ethyl (1RS,4RS,5RS)-4-(5-acetoxy-4,8-dimethyl-8-nonenyl)-4-methyl-3,8-dioxabicyclo[3.2.1]octane-1-acetate (13)

(Carbethoxymethylene)triphenylphosphorane (3.6 g, 10.3 mM) is added to 1RS,4RS,5SR-1-hydroxy-4-methyl-4-(5-acetoxy-4,8-dimethyl-8-nonenyl)-3,8-dioxabicyclo[3.2.1]octane (1.23 g, 3.47 mM). The mixture is heated under nitrogen to 120° C., stirred at this temperature for two days and then cooled to room temperature after which additional Wittig reagent (1.2 g, 3.4 mM) is added. The mixture is heated again under nitrogen to 120° C. and stirred at this temperature for two more days. The reaction mixture is then cooled to room temperature and extracted with a mixture of ether and hexane six times (1 ml ether and 20 ml hexane, each time). The combined extracts are evaporated in vacuo to give an oil (1.92 g). The crude reaction product is treated with petroleum-ether (30 ml of BP 30°-60° C. and filtered through Celite to give ethyl (1RS,4SR,5RS)-4-(5-acetoxy-4,8-dimethyl-8-nonenyl)-4-methyl-3,8-dioxabicyclo[3.2.1]octane-1-acetate (10.0 g, 68.7%).

TLC (10% ether in CH₂Cl₂): R$_f$=0.40. IR (neat) 1725 (CO), 1242 cm⁻¹ (acetate). NMR (CDCl₃,δ): 4.83 (m, 1H,

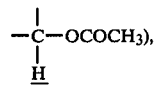

4.67 (m, 2H,

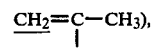

4.13 (q, J=7 Hz, 2H, —COOC<u>H</u>₂CH₃), 3.83 (m, 1H,

3.58 (q, J=11 Hz, 2H,

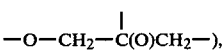

2.60 (s, 2H,

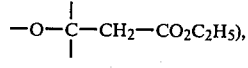

2.03 (s, 3H, —O—C<u>H</u>₃), 1.72 (br s, 3H,

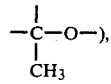

1.30 (s, 3H,

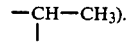

1.25 (t, J=7 Hz, 3H, —COOCH₂C<u>H</u>₃), 0.88 (d, J=7 Hz, 3H,

—C<u>H</u>—CH₃).

A sample (264 mg) is further purified by chromatography on SilicAR CC-7 (2.0 g). Elution with CH₂Cl₂ (500 ml) gives the faster running impurities (25 mg). Elution with 3% ether in CH₂Cl₂ (500 ml) gives ethyl (1RS,4SR,5RS)-4-(5-acetoxy-4,8-dimethyl-8-nonenyl)-4-methyl-3,8-dioxabicyclo[3.2.1]octane-1-acetate (89.1 mg, 35%).

EXAMPLE 16

Ethyl(1RS,4SR,5RS)-4-(5-acetoxy-4,8-dimethyl-7-nonenyl)-4-methyl-3,8-dioxabicyclo[3.2.1]octane-1-acetate (14)

p-Toluenesulfonic acid monohydrate (8.2 mg) is added to benzene (12 ml). The mixture is stirred and refluxed in a Dean-Stark apparatus and some of the benzene (4 ml) is drained from the side-arm. The bicyclic acetoxy ester, ethyl(1RS,4SR,5RS)-4-(5-acetoxy-4,8-dimethyl-8-nonenyl)-4-methyl-3,8-dioxabicyclo[3.2.1]octane-1-acetate (85 mg, 0.2 mM), dissolved in benzene (6 ml), is added at room temperature to the above mixture and the resultant mixture is stirred and refluxed (bath at 130° C.) for two hours. The temperature of the heating bath is then lowered to 90° C. and the stirring is continued at 90° C. for sixteen hours and then at room temperature for seventy-two hours. The reaction mixture is added to saturated NaHCO₃—H₂O (10 ml) and ether (20 ml). The organic layer is separated, washed with saturated NaCl—H₂O, dried with Na₂SO₄, filtered, and evaporated in vacuo to give ethyl(1RS,4SR,5RS)-4-(5-acetoxy-4,8-dimethyl-7-nonenyl)-4-methyl-3,8-dioxabicyclo[3.2.1]octane-1-acetate (80.4 mg, 95%).

TLC (10% ether in CH₂Cl₂): R_f=0.4. IR (neat) 1724 (CO), 1242 (acetate), 1087, 1060, 1020 cm⁻¹ (ether bonds). NMR (CDCl₃,δ): 5.12 (t, 1H,

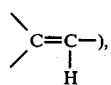

4.13 (q, J=7 Hz, 2H, —COOC<u>H</u>₂CH₃), 3.90 (m, 1H,

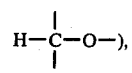

3.58 (q, J=11 Hz, 2H,

—O—CH₂—C(O)CH₂—), 2.65 (s, 2H,

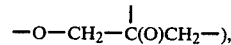

2.03 s, 3H, —O—CO—C<u>H</u>₃), 1.75 (br s, 3H,

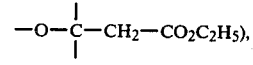

1.67 (br s, 3H,

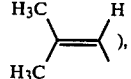

1.35 (s, 3H,

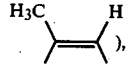

0.92 (d, J=7 Hz, 1H, —CH—C<u>H</u>₃). GS/MS (C.I mode) (M+1)⁺ 425→365 (base peak).

—HOAc

EXAMPLE 17

1RS,4SR,5RS-4-(4,8-dimethyl-5-hydroxy-7-nonen-1-yl)-4-methyl-3,8-dioxabicyclo[3.2.1]octane-1-acetic acid (I)

2 N NaOH-H₂O (2.0 ml) is added to ethyl (1RS,4SR,5RS)-4-(5-acetoxy-4,8-dimethyl-7-nonenyl)-4-methyl-3,8-dioxabicyclo[3.2.1]octane-1-acetate (79 mg, 0.19 mM) in methanol (2.0 ml) while stirring under nitrogen at 2° C. After ten minutes of stirring, it is allowed to come to room temperature and stirred under nitrogen for seventy-two hours. The methanol is evaporated in vacuo at room temperature and the residue is extracted with ether. The aqueous basic solution is cooled with ice water, stirred and acidified with 6 N HCl—H₂O, and extracted with ether. It is washed with saturated NaCl—H₂O, dried with Na₂SO₄, filtered, and evaporated in vacuo to give 1RS,4SR,5RS-4-(5-hydroxy-4,8-dimethyl-7-nonenyl)-4-methyl-3,8-dioxabicyclo[3.2.1]octane-1-acetic acid (66.9 mg, 91.3%).

TLC ether: petroleum-ether-AcOH (20:5:05): R_f=0.57. IR (neat) 3500–3300, 2500–2300 (OH), 1720 (CO, 1090, 1050, 1010 cm⁻¹ (ether bonds). NMR (CDCl₃,δ): 5.43 (br m, 2H, —O<u>H</u>+—CO₂<u>H</u>), 5.12 (t, 1H,

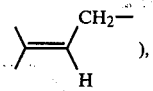

3.90 (m, 1H,

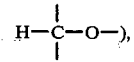

3.58 (q, J=11 Hz, 2H,

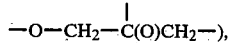

3.33 (m, 1H,

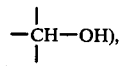

2.65 (br s, —C$\underline{H}_2$—CO$_2$H), 1.75 and 1.67 (2×br s, 2×3H, vinyl methyls), 1.35 (s, 3H,

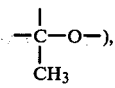

0.92 (d, J=Hz, 3H,

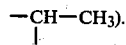

GC/MS of bis-TMS derivative M+ 498; M—C$_5$H$_9$=429; M—C$_5$H$_9$—TMSOH=339; BP=73.

EXAMPLE 18

(1RS,4SR,5RS)-4-(5-Hydroxy-4,8-dimethyl-8-nonenyl)-4-methyl-3,8-dioxabicyclo[3.2.1]octane-1-acetic acid Monohydrate (16)

2 N NaOH-H$_2$O (5.0 ml) is added to ethyl (1RS,4SR,5RS)-4-(5-acetoxy-4,8-dimethyl-8-nonenyl)-4-methyl-3,8-dioxabicyclo[3.2.1]octane-1-acetate (1.06 g, 2.5 mM) in methanol (5.0 ml) while stirring at 0° C. under nitrogen. The cooling bath is removed after fifteen minutes and the reaction is stirred at room temperature for three days. The methanol is evaporated in vacuo at room temperature and the residue is extracted with ether. The aqueous basic solution is cooled with ice water, stirred, acidified with 6 N HCl—H$_2$O, and extracted with ether. This extract is washed with saturated NaCl—H$_2$O, dried with Na$_2$SO$_4$, filtered, and evaporated in vacuo to give 608 mg (68.7%) of crude acid, which is purified by column chromatography on SilicAR CC-7. The acid is eluted with a mixture of petroleum ether and ether and acetic acid=150+50+1 ml; 200+200+2 ml; and 150+50+1 ml to give (1RS,4SR,5RS)-4-(5-hydroxy-4,8-dimethyl-8-nonenyl)-4-methyl-3,8-dioxabicyclo[3.2.1]octane-1 acid (305 mg):

IR (CHCl$_3$): 3000, 2800–2500 (shld), 1750, 1720, 1650, 730 cm$^{-1}$. NMR (CDCl$_3$): 6.10 (m, 2H, CO$_2$$\underline{H}$ and

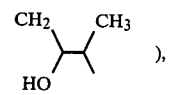

4.70 (m, 2H,

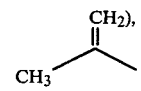

3.86–3.31 (m, 4H,

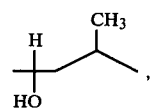

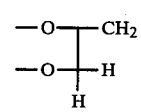

and

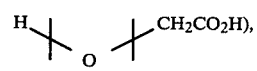

2.63 (m, 2H, C$\underline{H}_2$—CO$_2$H), 1.71 (br s, 3H,

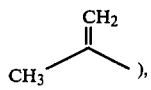

1.30 (s, 3H,

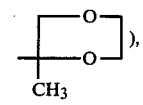

0.88 (d, J=6 Hz, 3H, —CHC$\underline{H}_3$—).

Preparation of ethyl 2,6-dimethyl-3-oxo-6-heptenoate

Sodium hydride (50% in mineral oil (7.68 g, 0.155 M) is treated with hexane to remove the mineral oil and suspended in tetrahydrofuran (300 ml). The suspension is cooled to +2° C. in an ice bath and to it is added dropwide ethyl 2-methylacetoacetate (22.8 ml, 0.158 M). Ten minutes after the addition is complete, n-butyllithium (2.4 M in hexane; 66.4 ml, 0.15 M) is added at +2° C. Ten minutes after this addition is complete, methallyl chloride (16 ml, 0.159 M) is added. The solution is stirred at 0° C. for ten minutes, acidified with 6 N HCl—H$_2$O and extracted with ether. The ether layer is separated and washed with saturated NaCl—H$_2$O, dried with Na$_2$SO$_4$, and the solvent evaporated in vacuo to afford a yellow oil. Fraction distillation affords 10.1 g (57%, based on recovered ethyl 2-methylacetoacetate) of ethyl 2,6-dimethyl-3-oxo-6-heptenoate as a colorless oil, BP 83°–85° C.1 mm.

IR (neat): 3080, 2980, 2960, 2900, 1745, 1725, 1650, 1450, 1180, 870 cm⁻¹. NMR (CDCl₃,δ): 1.27 (3H, t, J=7, C$\underline{H}$₃—H₂O); 1.37 (3$\underline{H}$, d, J=7 Hz,

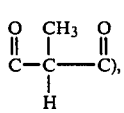

1.73 (3$\underline{H}$, br s,

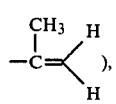

2.06-2.85 (4H, M,

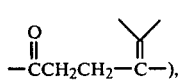

3.53 (1$\underline{H}$, dist. q, J=7.0 Hz,

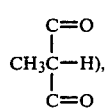

4.16 (2$\underline{H}$, q, J=7.0 Hz, OC$\underline{H}$₂—CH₃), 4.70 (2$\underline{H}$, m,

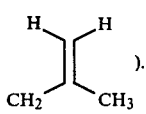

I claim:

1. The process for the preparation of a compound of the formula

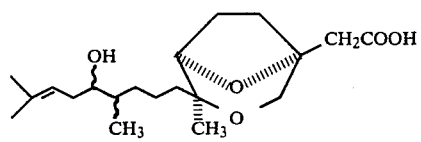

which comprises reacting a compound of the formula

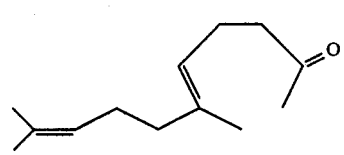

with trimethylsilyl chloride to form an enol silylether of the formula

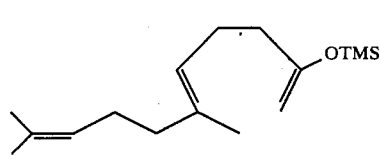

reacting the enol silylether with a brominating agent to form a bromide of the formula

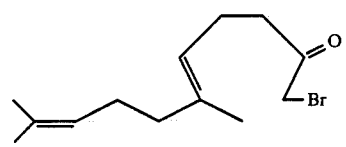

reacting the compound formed with a peroxy acid to form an epoxide of the formula

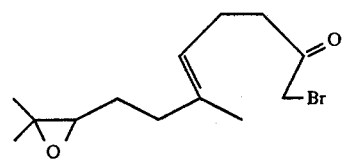

reacting the epoxide with periodic acid to form an aldehyde of the formula

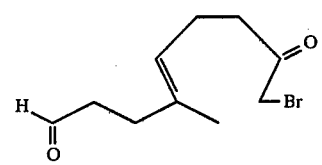

reacting the aldehyde with an oxidizing agent to form an acid of the formula

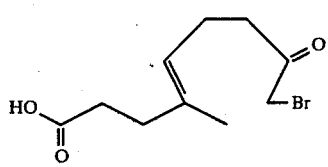

reacting the acid formed with a peroxy acid to form a bromo hemiketal γ-lactone of the formula

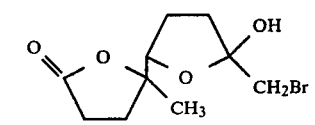

reacting the bromo hemiketal γ-lactone with a trialkyl orthoformate to form a mixture of the cis/trans-bromo ketal lactone of the formula

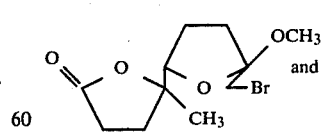
and
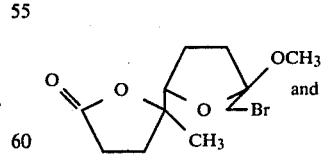

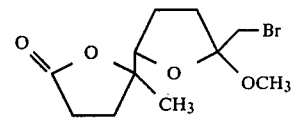

cyclizing the cis bromo ketal lactone with a cyclizing agent to form a bicyclic ketal acid of the formula

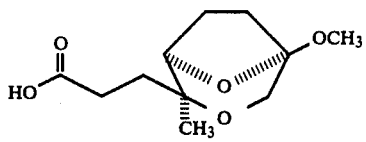

reacting the ketal acid with a first reducing agent to form an alcohol of the formula

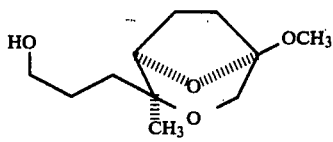

reacting the alcohol with methanesulfonyl chloride to form a mesylate of the formula

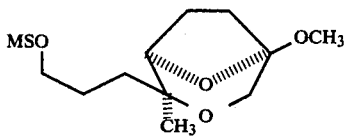

reacting the mesylate with a compound of the formula

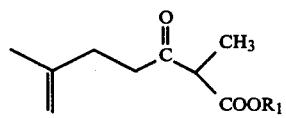

to form a condensation product of the formula

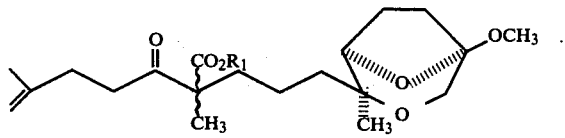

hydrolyzing and decarboxylating the carboxylic ester with a decarboxylating agent to form a ketone of the formula

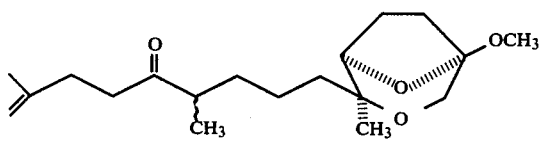

reducing the ketone with a second reducing agent to form an alcohol of the formula

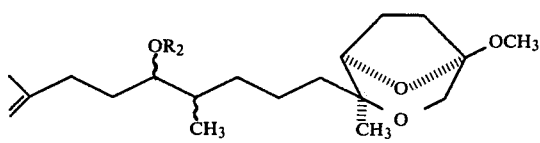

esterifying the alcohol with an esterifying agent to form an ester of the formula

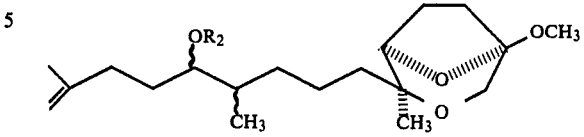

reacting the ketal with acid to form a hemiketal of the formula

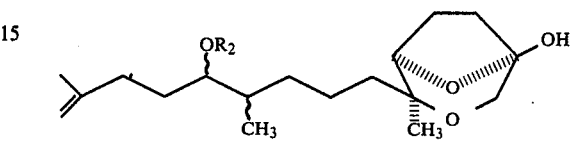

reacting the hemiketal with (carbethoxymethylene)triphenylphosphorane to form a compound of the formula

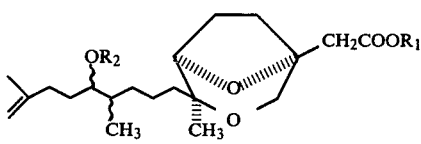

isomerizing the 8-nonenyl ester with an isomerizing agent to form a 7-nonenyl ester of the formula

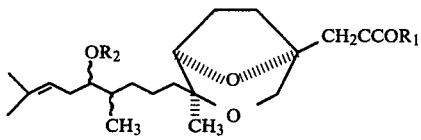

and hydroxyzing the esters with a hydrolyzing agent, wherein $R_1$ is hydrogen or a lower alkyl group having 1–5 carbon atoms, $R_2$ is hydrogen or lower acyl having 2–5 carbon atoms, TMS is a trimethylsilyl group and MS is a methylsulfonyl group.

2. The process of claim 1 wherein the brominating agent is N-bromosuccinimide.

3. The process of claim 1 wherein the oxidizing agent is $CrO_3$—$H_2SO_4$.

4. The process of claim 1 wherein the peroxy acid is m-chloroperbenzoic acid.

5. The process of claim 1 wherein the cyclizing agent is potassium hydroxide.

6. The process of claim 1 wherein the first reducing agent is diborane.

7. The process of claim 1 wherein the hydrolyzing and decarboxylating agent is sodium hydroxide.

8. The process of claim 1 wherein the second reducing agent is sodium borohydride.

9. The process of claim 1 wherein the esterifying agent is acetic anhydride.

10. The process of claim 1 wherein the acid is hydrochloric acid.

11. The process of claim 1 wherein the isomerizing agent is p-toluenesulfonic acid.

12. The process of claim 1 wherein the hydrolyzing agent is sodium hydroxide.

* * * * *